United States Patent
Conley et al.

(10) Patent No.: US 6,289,244 B1
(45) Date of Patent: Sep. 11, 2001

(54) SELF AUDIT SYSTEM

(75) Inventors: Vickie L. Conley, Woodbury; Allan T. Koshiol, Lino Lakes, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/378,593

(22) Filed: Aug. 20, 1999

(51) Int. Cl.[7] ............................................. A61N 1/37
(52) U.S. Cl. ................................. 607/27; 607/59
(58) Field of Search ................... 607/4, 5, 6, 8, 607/9, 27, 28, 32, 59, 60; 600/510

(56) References Cited

U.S. PATENT DOCUMENTS

| | | | |
|---|---|---|---|
| 4,825,869 | * 5/1989 | Sasmor et al. | 607/27 |
| 5,184,614 | 2/1993 | Collins et al. | 128/419 PG |
| 5,224,475 | 7/1993 | Berg et al. | 128/419 D |
| 5,344,430 | 9/1994 | Berg et al. | 607/8 |
| 5,404,877 | 4/1995 | Nolan et al. | 128/671 |
| 5,423,871 | 6/1995 | Hoegnelid et al. | 607/28 |
| 5,496,351 | 3/1996 | Plicchi et al. | 607/17 |
| 5,549,646 | 8/1996 | Katz et al. | 607/8 |
| 5,609,612 | 3/1997 | Plicchi et al. | 607/17 |
| 5,620,474 | 4/1997 | Koppman | 607/29 |
| 5,693,075 | 12/1997 | Plicchi et al. | 607/17 |
| 5,749,900 | 5/1998 | Schroeppel et al. | 607/4 |
| 5,755,742 | 5/1998 | Schuelke et al. | 607/27 |
| 5,814,088 | 9/1998 | Paul et al. | 607/28 |
| 5,876,353 | 3/1999 | Riff | 600/547 |
| 5,891,179 | 4/1999 | Er et al. | 607/27 |
| 5,897,577 | 4/1999 | Cinbis et al. | 607/28 |
| 5,957,861 | 9/1999 | Combs et al. | 600/547 |
| 6,016,447 | 1/2000 | Juran et al. | 607/27 |
| 6,016,448 | 1/2000 | Busacker et al. | 607/29 |
| 6,035,233 | 3/2000 | Schroeppel et al. | 600/515 |

FOREIGN PATENT DOCUMENTS

99/27992   6/1999   (WO) .............................. A61N/1/37

* cited by examiner

*Primary Examiner*—Jeffrey R. Jastrzab
(74) *Attorney, Agent, or Firm*—Schwegman, Lundberg, Woessner & Kluth, P.A.

(57) ABSTRACT

A self audit system for use in managing and monitoring measurements acquired by an implantable medical device in a period of time. The self audit system providing a system and method for, but not limited to, programming one or more valid ranges for one or more measurements acquired in an implantable medical device, acquiring one or more measurements in an implantable medical device, comparing the one or more measurements to their associated valid ranges, recording information about a measurement if it is not within its associated valid range and displaying a warning message if a measurement is not within its associated valid range.

22 Claims, 5 Drawing Sheets

SELF AUDIT SYSTEM

FIELD OF THE INVENTION

The present invention is related to a self audit system in a programmer for a implantable medical device, and more particularly to a self audit system that monitors and manages a plurality of measurements with associated ranges for the plurality of measurements in an implantable medical device.

BACKGROUND INFORMATION

Currently implantable medical devices acquire and store measurements from an implantable device in a patient. The measurements acquired by the implantable medical device are received by a programmer that displays the measurements. A user must then examine the measurements on the programmer to determine if the measurements are within appropriate limits for the patient. Manually examining the measurements usually consists of visually comparing measurements values to appropriate limits or ranges for the patient. The process of a user or physician manually examining measurements and comparing them to appropriate limits is time-consuming and tedious. In addition, important or useful data for the measurements is often overlooked when a user must manually compare the measurements to appropriate limits.

What is needed is a more efficient method of comparing measurements acquired by an implantable medical device to appropriate limits.

SUMMARY OF THE INVENTION

According to one aspect of the present invention, a self audit system is described for use in managing and monitoring measurements acquired by an implantable medical device in a period of time. The self audit system provides a system and method for, but is not limited to, programming one or more valid ranges for one or more measurements acquired in an implantable medical device, acquiring one or more measurements in an implantable medical device, comparing the one or more measurements to their associated valid ranges, recording information about a measurement if it is not within its associated valid range and displaying a warning message if a measurement is not within its associated valid range.

This summary is intended to provide a brief overview of some of the embodiments of the present system, and is not intended in an exclusive or exhaustive sense, and the scope of the invention is to be determined by the attached claims and their equivalents.

DETAILED DESCRIPTION

This detailed description provides a number of different embodiments of the present method. The embodiments provided herein are not intended in an exclusive or limited sense, and variations may exist in organization, dimension, software, design and configuration, without departing from the claimed invention, the scope of which is provided by the attached claims and equivalents thereof.

The leading digit(s) of reference numbers appearing in the figures generally corresponds to the figure number in which that component is first introduced, such that the same reference number is used throughout to refer to an identical component which appears in multiple figures. Signals and connections may be referred to by the same reference number or label, and the actual meaning will be clear from its use in the context of the description.

The present self audit system provides, among other things, a system and a method for monitoring and managing a plurality of measurements that have associated valid ranges in an implantable medical device. The self audit system includes a system and method for, but is not limited to, programming one or more valid ranges for one or more measurements acquired in an implantable medical device, acquiring one or more measurements in an implantable medical device, comparing the one or more measurements to their associated valid ranges, recording information about a measurement if it is not within its associated valid range and displaying a warning message if a measurement is not within its associated valid range. In one embodiment, the present self audit system is implemented in both an implantable medical device and a programmer for an implantable medical device. In alternate embodiments, the present self audit system is entirely separate in an implantable medical device.

Figure 1A:
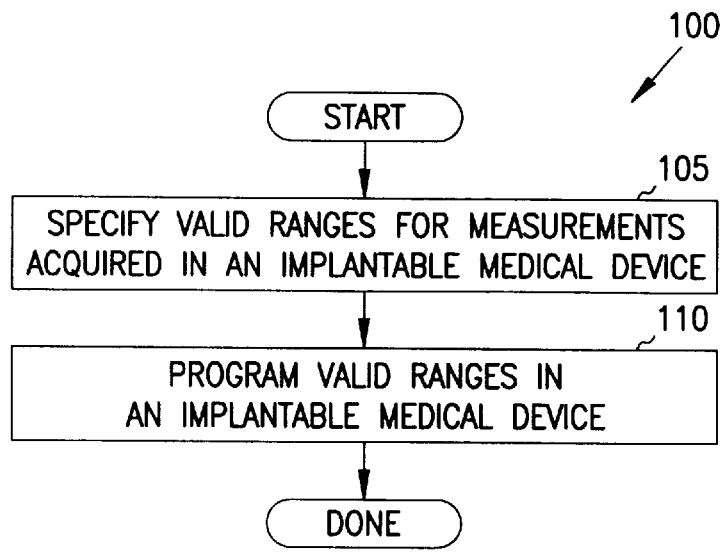
FIG. 1a shows one embodiment of a self audit system in a programmer.
Figure 1B:
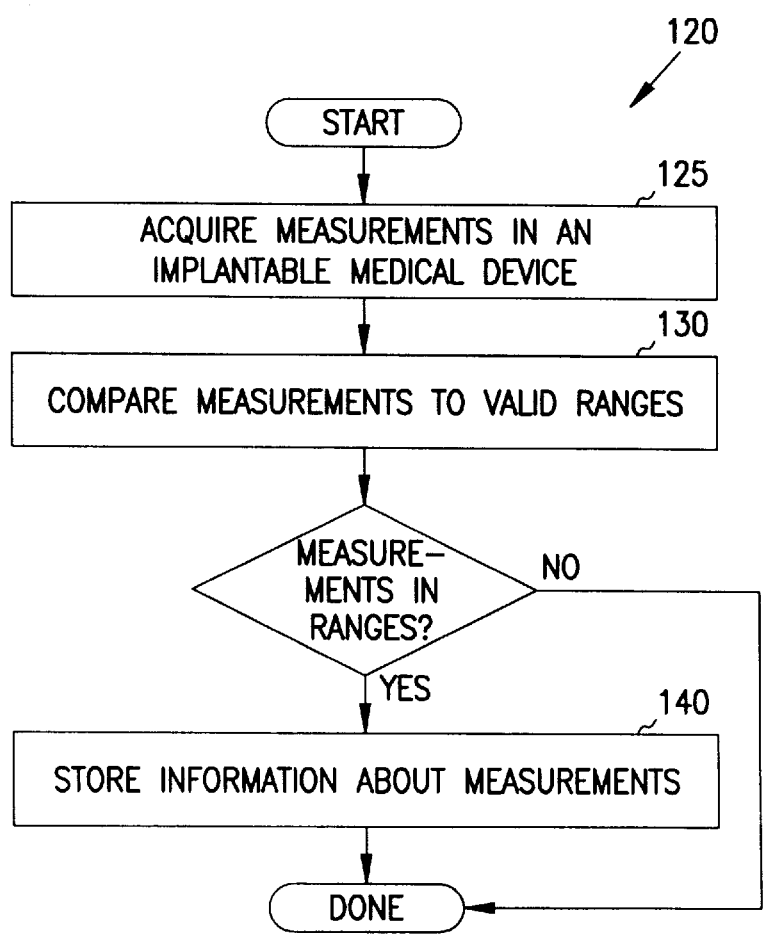
FIG. 1b shows one embodiment of a self audit system in an implantable medical device.
Figure 1C:
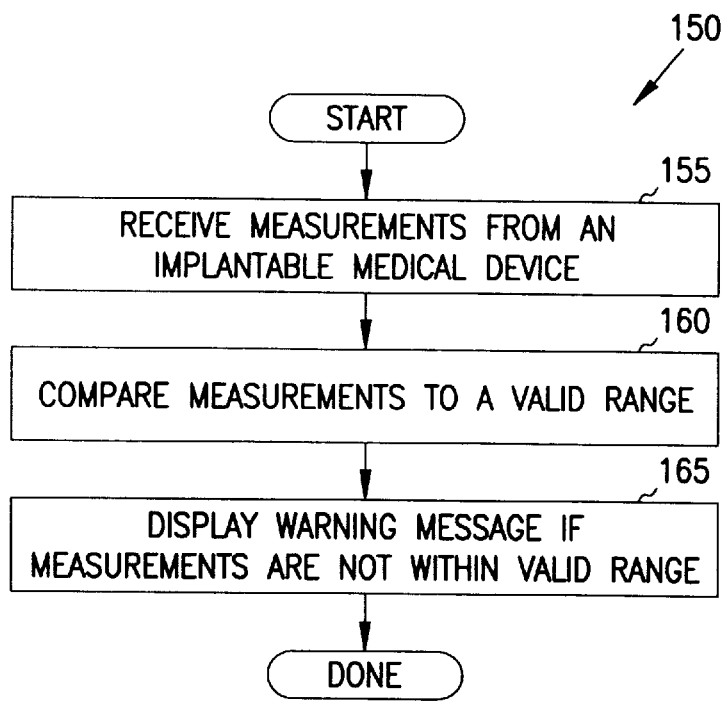
FIG. 1c shows one embodiment of a self audit system in a programmer.

FIG. 1a through 1c show examples of processes 100, 120, and 150 for the present self audit system. In one embodiment, shown in FIG. 1a, valid ranges are specified in a programmer for measurements that are acquired in an implantable medical device 105. In one embodiment, a valid range consists of a minimum value and a maximum value for one or more measurements acquired by an implantable medical device. In one embodiment, the plurality of measurements consist of atrial intrinsic amplitude measurements, ventricular intrinsic amplitude measurements, atrial pace impedance measurements, ventricular pace impedance measurements and shock impedance measurements. In step 110, a programmer programs the one or more valid ranges associated with the one or more measurements in an implantable medical device.

FIG. 1b shows a self audit system in an implantable medical device 120 for acquiring and comparing one or more measurements to one or more valid ranges programmed by a programmer. The plurality of measurements acquired in the implantable medical device are acquired in a period of time and compared to their associated valid ranges. In one embodiment, the period of time the measurements are acquired in the implantable medical device is on a daily basis. In alternate embodiments the measurements are acquired randomly, weekly, or any other period of time. The implantable medical device acquires one or more measurements 125. If the one or more measurements have a valid range, the implantable medical device compares these measurements to their associated valid ranges 130. Then, in one embodiment, if one or more measurements are not within their associated valid ranges the implantable medical device stores information related to the one or more measurements that are out of the valid range 140.

FIG. 1c shows a self audit system in a programmer for an implantable medical device 150 for receiving one or more measurements from an implantable medical device 155, comparing the one or measurements to a valid range 160, and displaying a warning message if the measurements are not within a valid range 165. In one embodiment, the one or more measurements received from the implantable medical device 155 are compared to the valid ranges associated with the one or more measurements. If one or more measurements are out of the valid range programmed in the implantable medical device. 110, the programmer displays a warning message 165. In one embodiment, the warning message consists of, but is not limited to, the date the measurement was taken and the value of the measurement. In one embodiment, the programmer compares the one or more measurements acquired in a implantable medical device to their associated valid ranges. In an alternate embodiment, the implantable medical device compares the one or more measurements to their associated valid ranges and stores specific information for each measurement if it is out of the valid range and sends the specific information to the programmer for the implantable medical device.

Figure 1D:
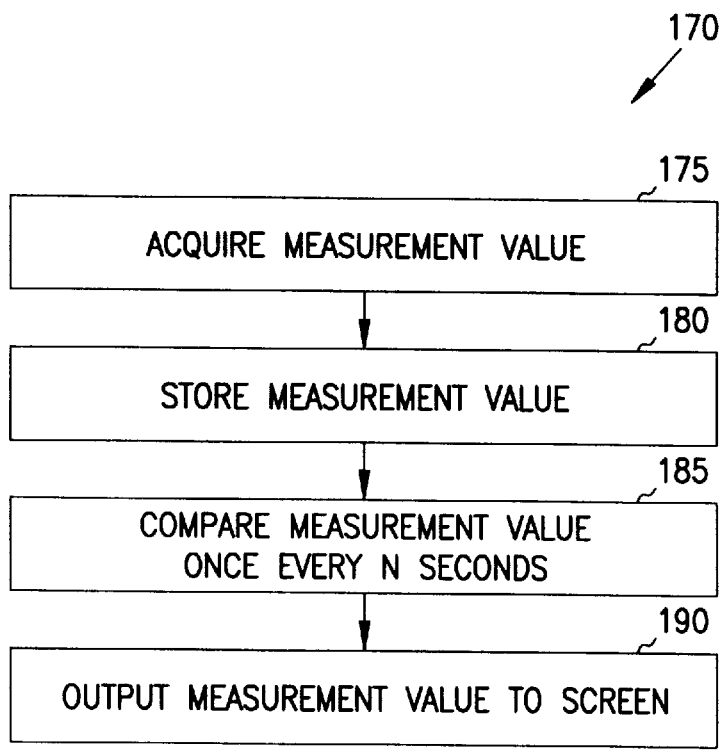
FIG. 1d shows one embodiment of a self audit system.

FIG. 1d shows one embodiment of steps 170 for the present self audit system. In one embodiment, the present self audit system acquires a measurement value 175, stores a measurement value 180, compares the measurement value once every N seconds 185 and outputs the measurement value to a programmer screen for an implantable device 190. In one embodiment, the self audit system acquires a measurement value from an implantable medical device 175 and stores the acquired value 180. The self audit system may acquire measurements from the implantable medical device at any time interval. In one embodiment, the measurements are acquired on a daily basis. In an alternate embodiment, the measurements are acquired on a random basis. After storing the acquired value 180, in one embodiment, the self audit system will then compare the measurement value once every N seconds 185 to a valid range that was specified for a particular measurement or set of measurements. In one embodiment, if the acquired measurement is out of the valid range, the self audit system outputs the measurement value to a programmer screen for an implantable medical device 190. In an alternate embodiment, the self audit feature outputs the measurement value to the screen 190 with all associated measurement data after comparing the measurement to its associated range.

Figure 2:
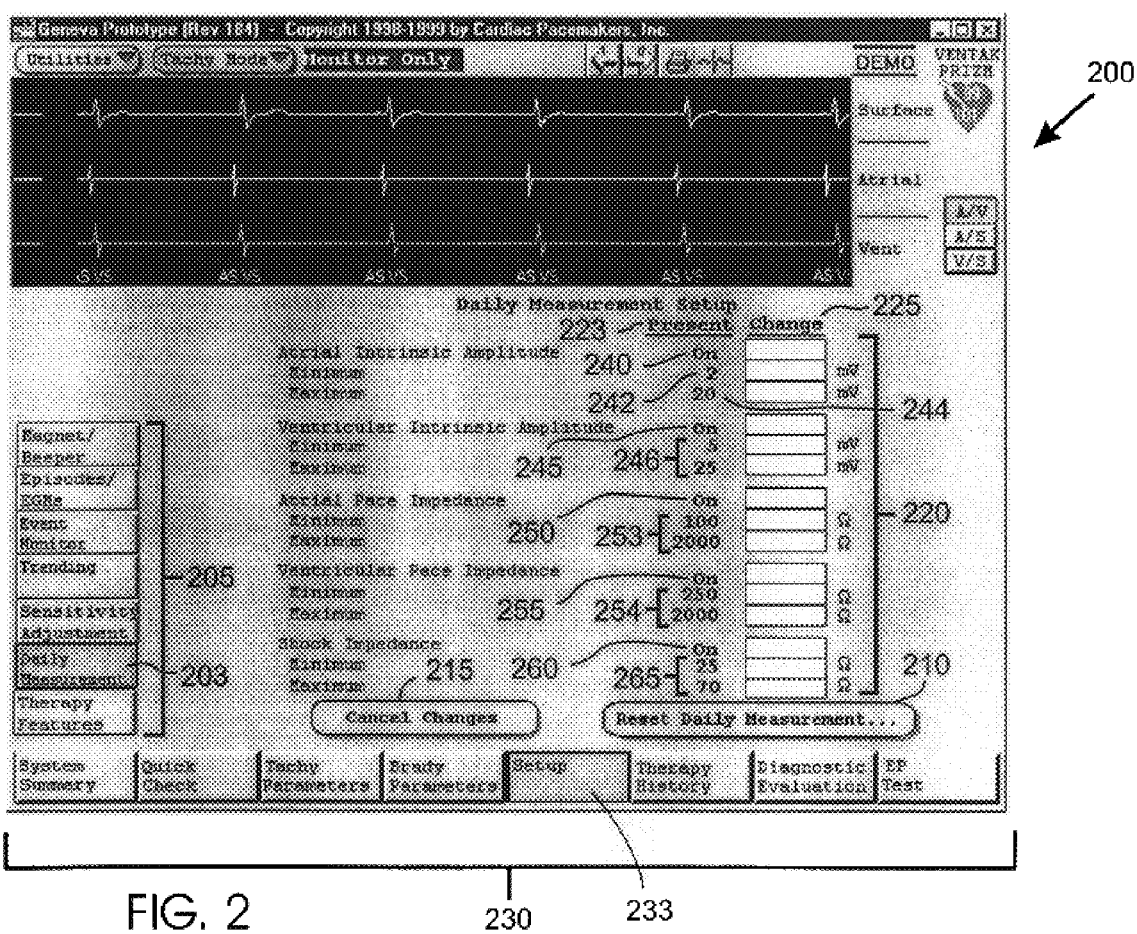
FIG. 2 shows one embodiment of a process for entering valid ranges for a plurality of measurements.

In one embodiment the present self audit system is implemented in an implantable medical device that is a defibrillator and a programmer. In one embodiment, the valid ranges for measurements acquired in the defibrillator on a daily basis are entered by using programmer screen 200 shown in FIG. 2. The programmer offers several options for programming, monitoring and managing a defibrillator in sections 205 and sections 230. In one embodiment, part of the self audit system is utilized on the programmer by selecting the daily measurement option 203 under the setup menu 233 to enter valid ranges for one or more measurements.

Valid ranges for measurements that have an associated valid range are entered in fields 220. In one embodiment, the daily measurements consist of atrial intrinsic amplitude measurements, ventricular intrinsic amplitude measurements, atrial pace impedance measurements, ventricular pace impedance measurements, and shock impedance measurements. Many other measurements may be acquired by the defibrillator as is apparent to one skilled in the art. In one embodiment, shown in fields 220, a valid range consists of a minimum and a maximum value for each measurement. Choosing option 210 on the program resets the values entered in fields 220. Choosing option 215 cancels the values entered in fields 220. The data shown under the present heading 223 represents current valid ranges for the daily measurements. For example the text in the same row as the atrial intrinsic amplitude measurements 240 indicates whether the atrial intrinsic amplitude measurements are to be acquired. In one embodiment, the text in field 240 is "On" and indicates that the atrial intrinsic amplitude measurements are being acquired in the defibrillator. In an alternate embodiment, the text in field 240 is "Off" and indicates that the atrial intrinsic amplitude measurements are not being acquired in the defibrillator. Fields 250, 255, and 260 also indicate whether the atrial pace impedance measurements, ventricular pace impedance measurements and shock impedance measurements respectively are being acquired in the defibrillator. The current valid range for the atrial intrinsic amplitude measurements is shown under heading 223 in fields 242 and 244. In one embodiment, the current minimum value for the atrial intrinsic amplitude measurements is 2 mV and the current maximum value is 20 mV, which arc shown in fields 242 and 244 respectively. Another example of a current valid range is shown on screen 200 in section 246 for the ventricular intrinsic amplitude measurements. In one embodiment, the valid range for the ventricular intrinsic amplitude measurements, which is shown in section 246, is from 5 mV to 25 mV. Similarly, in one embodiment, the current valid range for the atrial pace impedance measurements 253 is 100 Ohms to 2000 Ohms, the current valid range for the ventricular pace impedance measurements 254 is 250 Ohms to 2000 Ohms, and the current valid range for the shock impedance measurements 265 25 Ohms to 70 Ohms.

Figure 3:
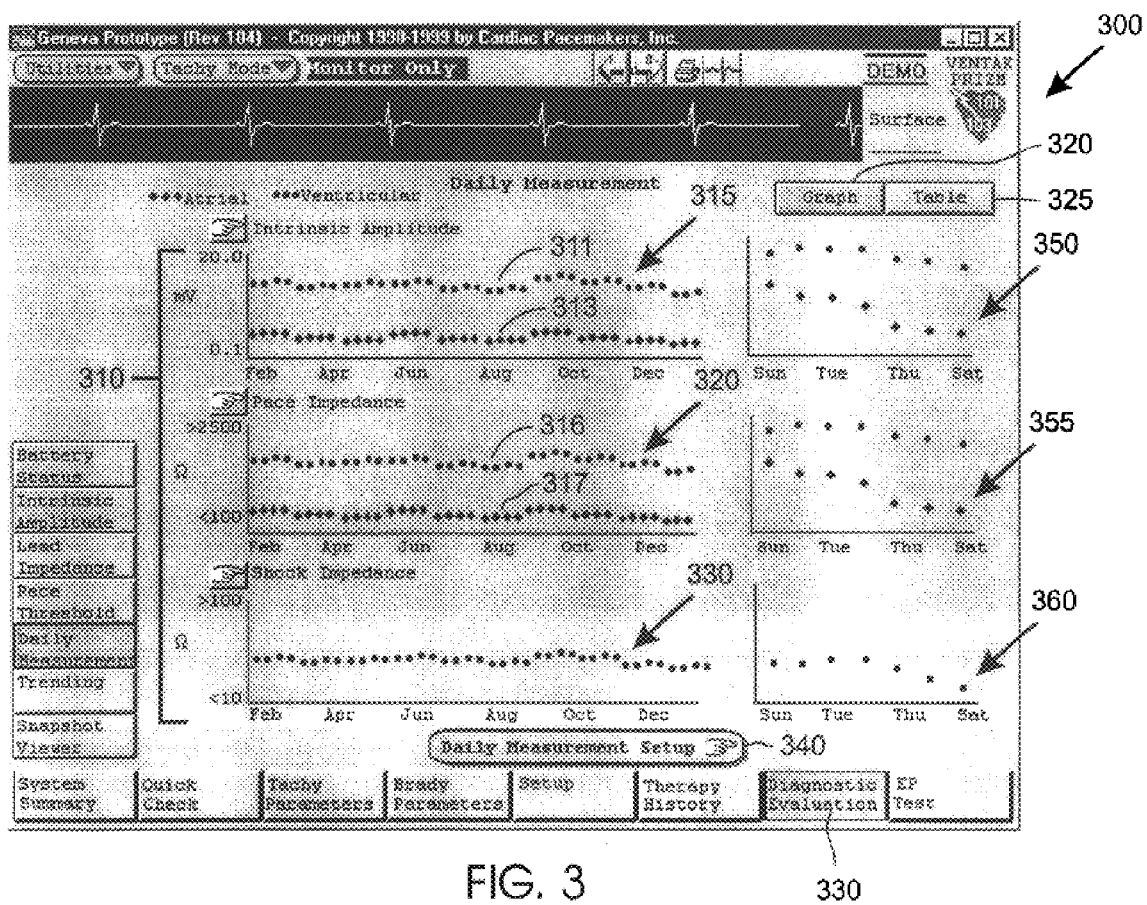
FIG. 3 shows one embodiment of displaying a plurality of measurements.

FIG. 3 shows one embodiment of a programmer screen 300 for a defibrillator, which is found by choosing menu option 330. In one embodiment, graphs of the daily measurements are displayed by choosing option 320. The graphs shown in section 310 represent data for the measurements received from the defibrillator. In one embodiment, the measurements represented in section 310 by graphs 315, 320 and 330 are the monthly intrinsic amplitude measurements, pace impedance measurements, and shock impedance measurements respectively. Graphs 315, 320, and 330 represent measurements data taken over a period of time. In one embodiment, the independent axes of graphs 315, 320 and 330 represent time and the dependent axes represent the values of the measurements. In one embodiment the dependent axis for the intrinsic amplitude measurements represent the measurement data in mV and the dependent axes for the pace impedance measurements and shock impedance measurements represent measurement data in Ohms. In one embodiment, graphs 314 and 320 have measurement data for both the atrial and ventricular chambers of the patient's heart. The atrial measurements for the intrinsic amplitude measurements are represented by curve 311 and the ventricular measurements are represented by curve 313. Similarly, the atrial measurements for the pace impedance measurements are represented by curve 316 and the ventricular measurements are represented by curve 310.

In one embodiment graphs 350, 355 and 360 represent the weekly measurement data for the intrinsic amplitude measurements, the pace impedance measurements, and the shock impedance measurements respectively. In alternate embodiments, the measurements represented in graphs 315, 320, 330, 350, 355, and 360 have other representations for the independent and dependent axes.

In an alternate embodiment, tables of the daily measurements are displayed by choosing option 325. In one embodiment, the tables for the daily measurements shows specific values for the daily measurements. In one embodiment option 320 was chosen and the programmer screen 300 shows graphs of the daily measurements acquired by the defibrillator. In one embodiment, the daily measurements shown on screen 300 are the intrinsic amplitude measurements, the pace impedance measurements, and the shock impedance measurements. Option 340 is chosen to return to programmer screen 200.

Figure 4:
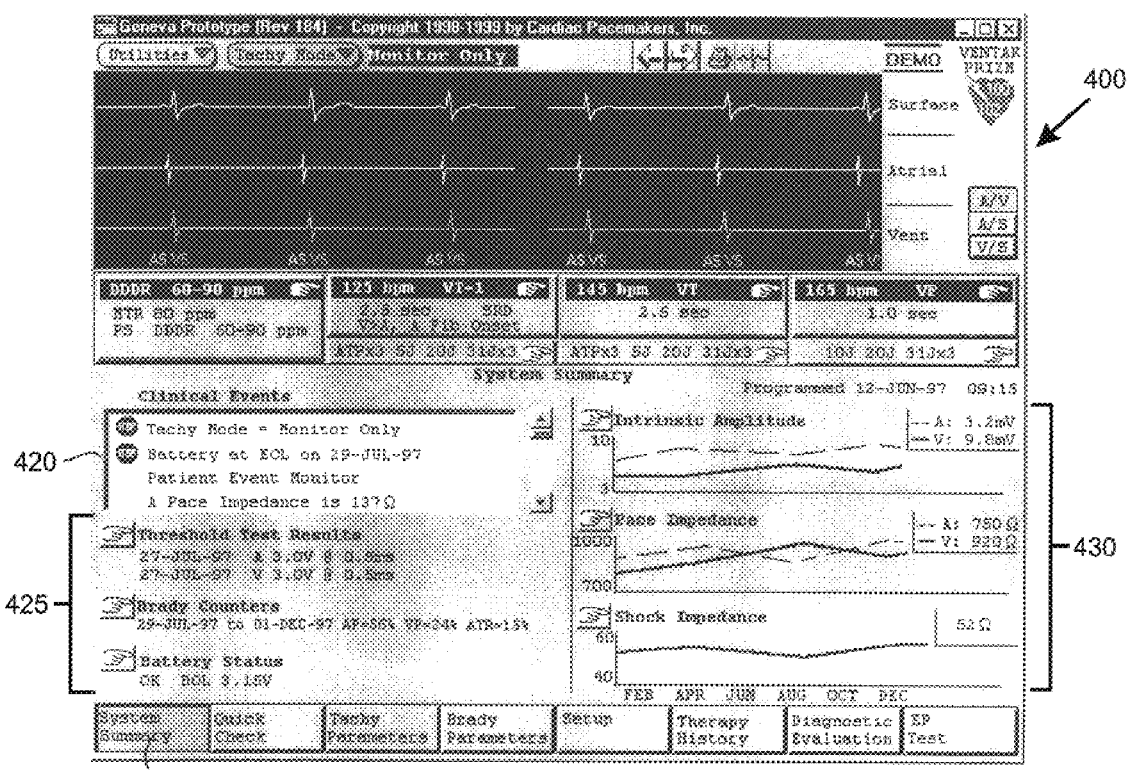
FIG. 4 shows one embodiment of a warning message displayed by a self audit system.

FIG. 4 shows one embodiment of a programmer screen 400, which is found by choosing menu option 410. In one embodiment, after the self audit system in the programmer receives the daily measurements from the defibrillator and compares the measurements to their associated valid ranges, the self audit system in the programmer displays the one or more measurements which were out of range in section 420. In one embodiment, section 420 shows specific information for one or more daily measurements that were out of range. Specific information may consist of, but is not limited to, the date the measurements that was out range was acquired and the value of the out of range measurement. Section 425 also shows specific information for daily measurements that were received from the defibrillator. Section 430 shows graphs of one or more of the daily measurements received from the defibrillator.

In an alternate embodiment, the present self audit system is implemented in an implantable medical device that is an implantable medical device.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
   receiving a plurality of measurements from an implantable medical device;
   displaying the plurality of measurements using a programmer having a graphical user interface for display and selection of a plurality of valid ranges for the plurality of measurements;
   comparing the plurality of measurements to selected valid ranges for the plurality of measurements; and
   displaying a warning message if one or more of the plurality of measurements are not within the valid range.

2. The method of claim 1, wherein the plurality of measurements are acquired daily.

3. The method of claim 1, wherein the plurality of measurements are acquired at random time intervals.

4. The method of claim 1, wherein the implantable medical device is a cardiac pacing device.

5. The method of claim 1, wherein the implantable medical device is a defibrillator.

6. The method of claim 1, wherein the plurality measurements consist of one or more atrial intrinsic amplitude measurements, one or more ventricular intrinsic amplitude measurements, one or more atrial pace impedance measurements, one or more ventricular pace impedance measurements, and one or more shock impedance measurements.

7. The method of claim 1, wherein the plurality of measurements consist of one or more atrial intrinsic amplitude measurements, one or more ventricular intrinsic amplitude measurements, one or more atrial pace impedance measurements, one or more ventricular pace impedance measurements, and one or more shock impedance measurements.

8. A programming apparatus for programming an implantable medical device, comprising:
   a graphical user interface for selecting a plurality of valid ranges for a plurality of measurements in the implantable medical device;
   communication means for acquiring the plurality of measurements;
   processing means for analyzing the plurality of measurements and for comparing the plurality of measurements to a selected valid range; and
   display means for displaying the plurality of measurements and for displaying a warning message if any of the plurality of measurements are not within the selected valid range.

9. The apparatus of claim 8, wherein the implantable medical device is a cardiac pacing device.

10. The apparatus of claim 8, wherein the implantable medical device is a defibrillator.

11. The apparatus of claim 8, wherein the plurality of measurements are acquired daily.

12. The apparatus of claim 8, wherein the plurality of measurements are acquired at random time intervals.

13. A programming apparatus for programming an implantable medical device, comprising:
   a communication device;
   a display device that provides a graphical user interface for displaying and selecting a plurality of valid ranges for a plurality of measurements in an implantable medical device;
   a processor connected to the communication device and the display device, wherein the processor acquires the plurality of measurements using the communication device from the implantable medical device, compares the plurality of measurements to a selected valid range and displays a warning message on the display device if one or more of the plurality of measurements are not within the selected valid range.

14. The apparatus of claim 13, wherein the implantable medical device is a cardiac pacing device.

15. The apparatus of claim 13, wherein the implantable medical device is a defibrillator.

16. The apparatus of claim 13, wherein the plurality of measurements are acquired daily.

17. The apparatus of claim 13, wherein the plurality of measurements are acquired at random time intervals.

18. A method comprising:
   programming a plurality of measurements to be performed in an implantable device using a programmer having a graphical user interface for display and selection of a plurality of valid ranges for the plurality of measurements;
   receiving the plurality of measurements from an implantable medical device;
   comparing the plurality of measurements to selected valid ranges for the plurality of measurements; and
   displaying a warning message if one or more of the plurality of measurements are not within the valid range.

19. The method of claim 18, further comprising selecting the plurality of valid ranges for a specific patient.

20. The method of claim 18, wherein displaying a warning message includes displaying a date, time and measurement for the plurality of measurements that are not within the valid range.

21. The method of claim 20, wherein the implantable medical device records the date, time and measurement for the plurality of measurements that are not within the valid range.

22. The method of claim 20, wherein the plurality measurements consist of one or more atrial intrinsic amplitude measurements, one or more ventricular intrinsic amplitude measurements, one or more atrial pace impedance measurements, one or more ventricular pace impedance measurements, and one or more shock impedance measurements.

* * * * *